US012805965B2

(12) United States Patent
Santek et al.

(10) Patent No.: US 12,805,965 B2
(45) Date of Patent: Nov. 24, 2026

(54) VIDEO GLASSES FOR USE WITH A STEREOSCOPIC MICROSCOPE FOR MICROSURGICAL PROCEDURES ON PATIENTS

(71) Applicant: BHS Technologies GmbH, Innsbruck (AT)

(72) Inventors: Michael Santek, Götzens (AT); Gregor Burger, Völs (AT); Mark Capelli, Innsbruck (AT); Markus Friedrich Hütter, Zirl (AT)

(73) Assignee: BHS Technologies GmbH, Innsbruck (AT)

( * ) Notice: Subject to any disclaimer, the term of this patent is extended or adjusted under 35 U.S.C. 154(b) by 708 days.

(21) Appl. No.: 17/614,639

(22) PCT Filed: May 26, 2020

(86) PCT No.: PCT/AT2020/000011
§ 371 (c)(1),
(2) Date: Nov. 29, 2021

(87) PCT Pub. No.: WO2020/237267
PCT Pub. Date: Dec. 3, 2020

(65) Prior Publication Data

US 2022/0226064 A1 Jul. 21, 2022

(30) Foreign Application Priority Data

May 29, 2019 (AT) .................................. A 204/2019

(51) Int. Cl.
*A61B 90/25* (2016.01)
*G02B 27/01* (2006.01)
(Continued)

(52) U.S. Cl.
CPC .......... *A61B 90/25* (2016.02); *G02B 27/0176* (2013.01); *A61B 2034/2055* (2016.02);
(Continued)

(58) Field of Classification Search
CPC ............ A61B 90/25; A61B 2034/2055; A61B 2090/368; A61B 2090/3937;
(Continued)

(56) References Cited

U.S. PATENT DOCUMENTS 5,412,811 A 5/1995 Hildenbrand et al.
5,506,730 A * 4/1996 Morley .................... A42B 3/04 2/6.2

(Continued)

FOREIGN PATENT DOCUMENTS

AT 519845 10/2018
CN 204883055 12/2015

(Continued)

OTHER PUBLICATIONS

Notification of Office Action and Search Report Dated Aug. 12, 2023 From the China National Intellectual Property Administration Re. Application No. 202080038394.3 and Its Translation Into English. (19 Pages).

(Continued)

*Primary Examiner* — Sharrief I Broome
*Assistant Examiner* — Journey F Sumlar

(57) ABSTRACT

Video glasses for microsurgical procedures include a support device to fasten the glasses to a user's head and an image display unit for outputting images. A joint with a rotational axis connects the support device to the image display unit, allowing rotation between an operating position in front of the user's eyes and an upward rest position outside the user's visual field. A locking device includes a latching device and a catch. Upon rotation in a first direction,
(Continued)

the latching device engages the catch in a holding position. Further continued rotation in the same direction releases the latching device. Rotation in the opposite direction is impeded while engaged and cannot release the mechanism. Consequently, unintended movement of the image display unit from the rest position during surgery is prevented by requiring the continued forward rotation before release can occur.

18 Claims, 6 Drawing Sheets

(51) Int. Cl.
*A61B 34/20* (2016.01)
*A61B 90/00* (2016.01)

(52) U.S. Cl.
CPC . *A61B 2090/368* (2016.02); *A61B 2090/3937* (2016.02); *A61B 2090/3979* (2016.02); *G02B 2027/0159* (2013.01); *G02B 2027/0178* (2013.01)

(58) Field of Classification Search
CPC . A61B 2090/3797; A61B 90/30; A61B 90/36; A61B 90/361; A61B 90/3612; G02B 2027/0159; G02B 2027/0178
See application file for complete search history.

(56) References Cited

U.S. PATENT DOCUMENTS

| | | | | |
|---|---|---|---|---|
| 5,579,026 | A * | 11/1996 | Tabata | G09G 5/399 345/8 |
| 5,581,806 | A | 12/1996 | Capdepuy et al. | |
| 5,767,820 | A | 6/1998 | Bassett et al. | |
| 5,954,642 | A | 9/1999 | Johnson et al. | |
| 6,105,909 | A * | 8/2000 | Wirth | F16M 11/126 359/384 |
| 9,318,077 | B2 * | 4/2016 | Kobayashi | G09G 3/003 |
| 2002/0120979 | A1 | 9/2002 | Prendergast | |
| 2004/0070823 | A1 | 4/2004 | Radna | |
| 2005/0063047 | A1 | 3/2005 | Obrebski et al. | |
| 2007/0114252 | A1 | 5/2007 | Gruebel et al. | |
| 2010/0026970 | A1 * | 2/2010 | Tanaka | H04N 5/74 351/158 |
| 2010/0299814 | A1 | 12/2010 | Celona et al. | |
| 2010/0321409 | A1 * | 12/2010 | Komori | G06T 3/40 345/656 |
| 2013/0043250 | A1 * | 2/2013 | Kreidler | A61L 2/26 292/286 |
| 2016/0225192 | A1 | 8/2016 | Jones et al. | |
| 2017/0153862 | A1 | 6/2017 | Serota | |
| 2018/0299681 | A1 | 10/2018 | Eastwood et al. | |
| 2019/0037715 | A1 | 1/2019 | Chen et al. | |
| 2020/0333578 | A1 | 10/2020 | Capelli et al. | |

FOREIGN PATENT DOCUMENTS

| | | | | |
|---|---|---|---|---|
| CN | 107465895 | | 12/2017 | |
| DE | 3523446 | A1 * | 1/1987 | H01R 4/483 |
| DE | 695 03 078 | | 10/1998 | |
| DE | 102018204925 | | 10/2018 | |
| EP | 0535552 | | 9/1992 | |
| WO | WO 2010/126441 | | 11/2010 | |
| WO | WO 2016/143279 | | 9/2016 | |
| WO | WO 2018/170522 | | 9/2018 | |
| WO | WO-2018170522 | A1 * | 9/2018 | G02B 21/362 |
| WO | WO 2020/237267 | | 12/2020 | |

OTHER PUBLICATIONS

International Search Report and the Written Opinion Dated Nov. 16, 2020 From the International Searching Authority Re. Application No. PCT/AT2020/000011 and Its Translation of Search Report Into English. (14 Pages).

* cited by examiner

VIDEO GLASSES FOR USE WITH A STEREOSCOPIC MICROSCOPE FOR MICROSURGICAL PROCEDURES ON PATIENTS

RELATED APPLICATIONS

This application is a National Phase of PCT Patent Application No. PCT/AT2020/000011 having International filing date of May 26, 2020, which claims the benefit of priority of Austrian Patent Application No. A 204/2019 filed on May 29, 2019. The contents of the above applications are all incorporated by reference as if fully set forth herein in their entirety.

FIELD AND BACKGROUND OF THE INVENTION

The present invention relates to video glasses for use with a stereoscopic microscope for microsurgical procedures on patients.

Microscope-assisted surgery operation is known in the field of surgery of small structures, for example in neurosurgery or procedures on the ossicles in the middle ear, as well as in implant surgery. Thereby, the area to be treated, referred to in the following as the area of intervention, on the patient, at which the microsurgical procedure is to be performed, is represented, preferably by video glasses, in a magnified manner with the aid of a microscope.

From the pending patent application AT519845 by the inventors, video glasses for use with a stereoscopic microscope are known. It has turned out that the additional provision of the option to manually pivot the image display unit out and in the visual field of the surgeon wearing the video glasses without significant resistance and simultaneously the requirement to hold the image display unit stable in an upwardly pivoted state are not compatible or only implementable by an additional complex control circuit with sensors and drives, respectively.

Therefore, there is a demand to provide video glasses with an easy and without significant resistance at any time manually pivotable image display unit, while simultaneously keeping the image display unit in a stable position in at least one holding position even during fast movements of the surgeon wearing the video glasses and therefore high acceleration and centrifugal forces occurring thereby.

SUMMARY OF THE INVENTION

The objective is achieved by the video glasses according to the invention according to the features of claim 1. Advantageous modifications are specified in the dependent claims 1 to 14. Claim 15 specifies a stereoscopic microscope according to the invention.

Video glasses for use in microsurgical procedures according to the invention comprise a support device configured to fasten the video glasses to a head of a user, an image display unit for outputting images, a joint with a rotational axis, which connects the support device with the image display unit rotationally about the rotational axis between an operating position, in which the image display unit is arranged in front of the eyes of the user and images can be displayed to the user, and a rest position, in which the image display unit is arranged upwards out of the visual field of the user, and a locking device comprising a latching device and a catch arranged to let the latching device upon rotation in a rotational direction about the rotational axis engage the catch in a holding position and to release the latching device from the catch upon further rotation in the rotational direction, and wherein a rotation in the opposite rotational direction beyond the holding position is impeded as long as the latching device is engaged in the catch.

In an embodiment, the holding position corresponds to the rest position and/or the locking device comprises at least a further holding position between the rest position and the operating position. In an advantageous embodiment, the rotational angle from the holding position until release of the latching device from the catch is at least 10°. In a further advantageous embodiment, the rotational angle may be not more than 15° or is in a range from 10° to 15°.

The latching device may be configured as an elastically deformable tongue, and may be integrally made of plastic with the support device in a further advantageous embodiment. In an alternative embodiment, the latching device may comprise a pin biased by a spring and rotationally supported.

In a further preferred embodiment, the locking device is configured to only impede a rotation in the opposite rotational direction beyond the holding position in the rotational direction from the operating position in the rest position in the engaged state. In an embodiment, this may be achieved by the latching device comprising a pin rounded at one side and by the catch configured to let the rounded pin slide off the catch upon rotation in the opposite rotational direction.

The video glasses according to the invention may comprise a catch configured as notch. Said catch may be applied at a tip of a nose. In a preferred modification of the video glasses, the joint is a parallelogram joint. The video glasses according to the invention may further comprise an orientation sensor. The stereoscopic microscope according to the invention comprising video glasses according to the invention.

DESCRIPTION OF SPECIFIC EMBODIMENTS OF THE INVENTION

Preferred embodiments of the video glasses 105 according to the invention for use with a stereoscopic microscope 100 in microsurgical procedures are described below with reference to the accompanying figures.

Figure 1:
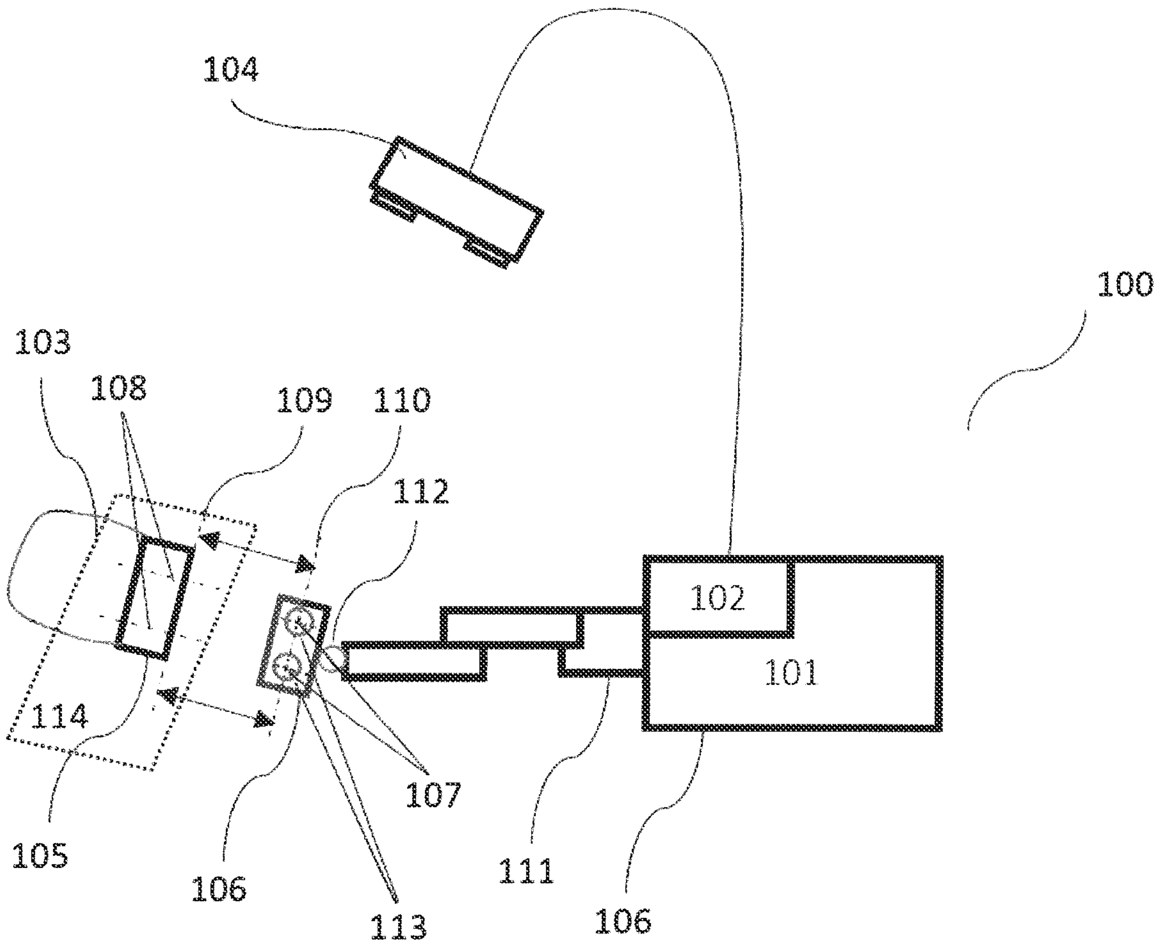
FIG. 1 shows a microsurgical stereoscopic microscope in an embodiment for use of the video glasses according to the invention.

FIG. 1 shows schematically the design of a stereoscopic microscope 100 by the inventors in the pending patent application with the application no. PCT2019AT000005 in plan view for use in microsurgical procedures, with which the video glasses according to the invention may be preferably used. The stereoscopic microscope 100 comprises a stand 106 pivotally connectable with a robotic arm 111 via a joint 112. The robotic arm 111 is affixable in a stable manner on the floor of the operating room via a holding device 106 to avoid vibrations to the greatest extent. Two optical image capturing units 113 are connectable to the stand 106 such that a stereoscopic image of the area of intervention 117 on the patient to be displayed during use can be captured and to define an image acquisition plane 110 by the two optical axis 107 of the image capturing units 113. The image capturing units 113 are configured to enable an optical magnification up to 100 times. In an advantageous embodiment, the image capturing units 113 may be additionally configured to enable optical zoom-out. This is particularly advantageous for the user 103, since he may get an overview of the area of intervention 117 and beyond. It also helps the user 103 to orient himself when approaching the area of intervention 117 with the surgical tools in hands. The images captured by both image capturing units 113 are transmitted and displayed by video glasses 105 comprising an optical image display unit 115 with a display to display an image to a user 103 wearing the video glasses 105. For the stereoscopic correct and for the natural eye-hand-coordination required orientation of the images displayed to the user, the stereoscopic microscope comprises a detection device 104, which detects the spatial orientation of the video glasses 105.

Figure 2:
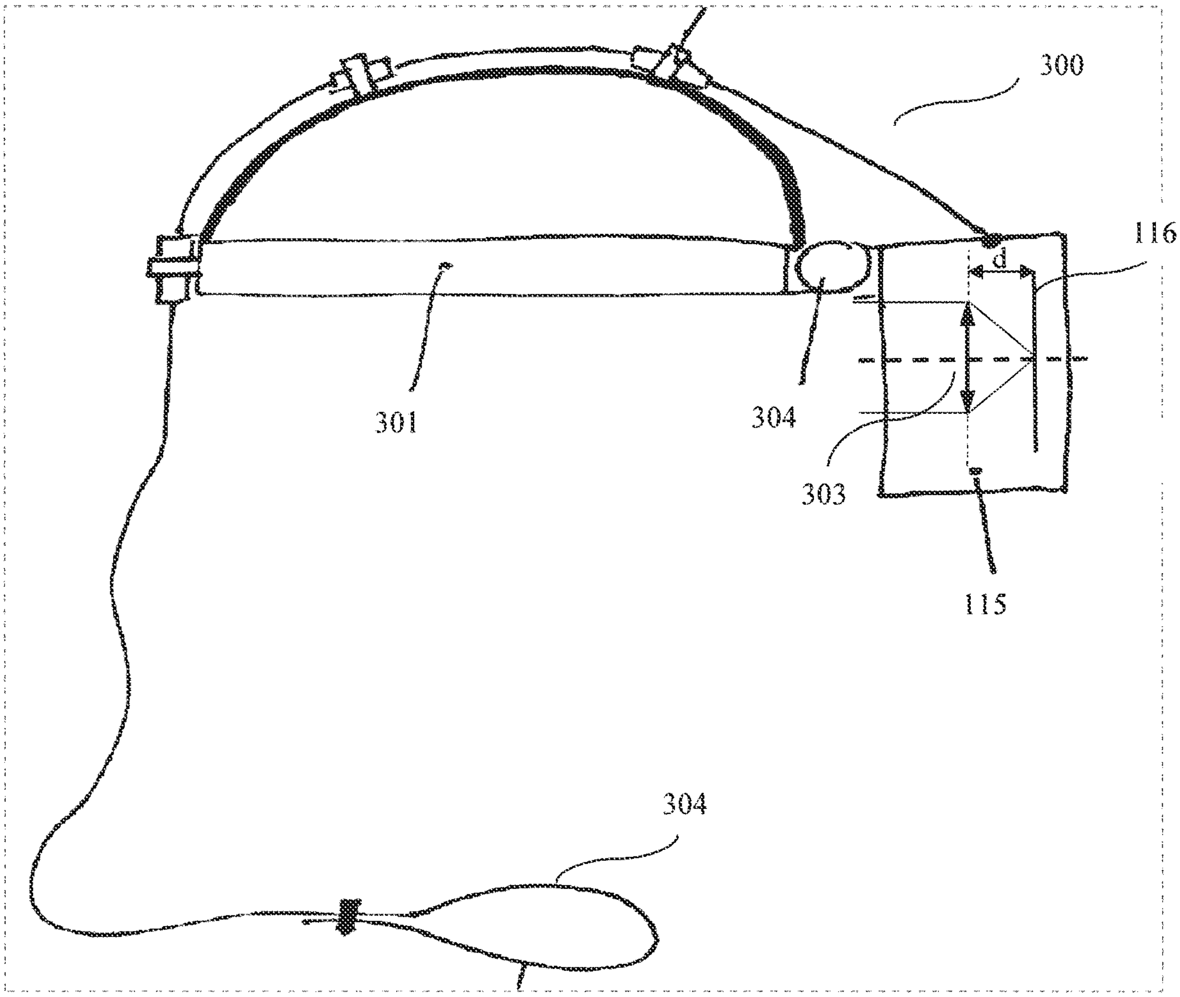
FIG. 2 shows video glasses known from the prior art.

FIG. 2 shows video glasses 300 with a support device 301 to hold the video glasses 300 on the head of the user 103 as known from the patent application of the inventors AT519845. The image display unit 115 is rotatably connected to a rotational axis 302 with respect to the support device 301 via joint 304. The video glasses 300 additionally comprise a cable control 304, which forms a manually operable loop with one end and which is affixed to the image display unit 115 with the other end such that the image display unit 115 is upwardly pivotable about the rotational axis 302 by the joint 304 to be guidable out of the visual filed of the user 103 wearing the video glasses 300 into the rest position. In the embodiment shown in FIG. 2, this is done by shortening the cable length by pulling on the cable control 304. Thereby, the image display unit 115, which is initially arranged in front of the eyes of the user 103 wearing the video glasses 300 and is in the operating position, is pivoted upwardly via the joint 304 about the rotational axis 302 above the eyes and therefore out of the visual field of the user 103 in the rest position against the weight force F. Conversely, if the cable length is lengthened, the image display unit 115 pivots back from the rest position in the operating position due to the weight force F. The video glasses 300 according to the invention are by no means limited to this embodiment, in particular other drives and also manual interventions are possible to guide the image display unit 115 out of the visual field of the user into the rest position (not shown) and vice versa from the rest position into the operating position. The image display unit 115 comprises image display devices 116 and a converging lens 303 for each eye of the user. The image display devices 116 of the image display unit 115 are arranged in a plane forming the image plane 109 and may be configured as either a single display, wherein the image output on the display is being divided for each image display unit 115, or as two separate displays.

Figure 3:
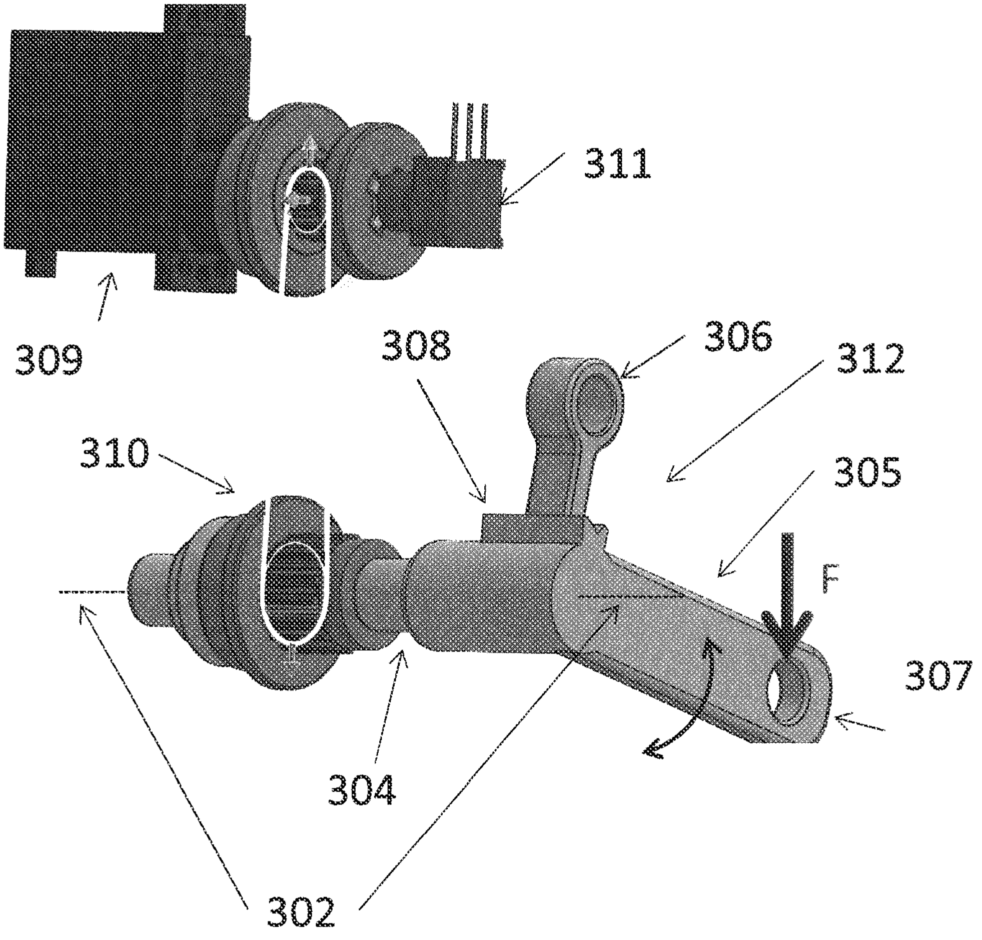
FIG. 3 shows video glasses in an embodiment preferred for the stereoscopic microscope according to the invention.

FIG. 3 shows an embodiment of the locking device 312 of the video glasses 300 according to the invention by way of example. Thereby, the joint 304 with the rotational axis 302 is affixed on one side via the lever arm 305 to the image display unit 115 via a mechanical connection 307. The joint 304 is on the other side affixed to the support device 301 not shown such that a rotation of the joint 304 about the rotational axis 302 pivots the image display unit 115 relatively to the support device 301. If, as shown in the Figure, the joint 304 is a rotational joint, the image display unit 115 is thereby pivoted about the joint axis 302. If, in an embodiment, the joint 304 is configured as parallelogram joint (not shown), the image display unit 115 moves along a circular path without itself rotating about the rotational axis 302. Therefore, the image display unit 115 may come to rest closer to the user's head in the rest position, forms a shorter lever, and advantageously allows a lower torque to be effective on the user's head. This increases the comfort of wear of the video glasses 300 in the rest position.

In a preferred embodiment, the video glasses 300 according to the invention comprise an electric drive 309, which establishes a rotatable connection with the joint 304 via a sliding clutch 310. The sliding clutch 310 has thereby the function not to stop the electric drive 309 when the image display unit 115 is in the rest position or in the operating position to avoid high currents by the electric drive 309. Additionally, the sliding clutch 310 helps to reduce the force to be applied for the manual rotation of the image display unit 115. For example, the force to be applied by the user 103 to move the image display unit 115 upwardly from the operating position into the rest position is only slightly greater than the weight force F. Further, the sliding clutch 310 improves safety, if the image display unit 115 is blocked in an intermediate position between the operating position and the drive position, to avoid, on one hand, too high currents by the electric drive 309 as before and, on the other hand, to prevent the user 103 from becoming trapped. The rotatable connection may either take place by direct connection of the joint 304 and the electric drive 309, or by an intermediate reduction gear comprising intermeshing gears or belts or a combination of gears and belts. In an embodiment, the electric drive 309 may be configured as a servo motor.

In an advantageous embodiment according to the invention, the electric drive 309 is affixed to the support device 301 and drives the portion of the joint 304 affixed to the image display unit 115. This embodiment provides the advantage that the weight of the image display unit 115 may be decreased and therefore contributes to the ability to pivot the image display unit 115 with less force effort by the electric drive 309 as well as manually. However, the electric drive 309 may just also be affixed to the image display unit 115, wherein, in such event, the respective portion of the joint 304 which is connected to the support device 301 is driven. In order to control the position of the image display unit 115 with respect to the support device 301, a sensor 311 may be mounted on the rotational axis of the electric drive 309 or the rotational axis 302 of the joint 304. In an embodiment, the sensor 311 may be a rotation rate sensor or a rotatable resistor.

The locking device 312 comprises a latching device 306 and a catch 308 arranged to let the latching device 306 upon rotation in a rotational direction about the rotational axis 302 of the joint 304 engage the catch 308 in the holding position such that thereby a rotation in the opposite direction beyond the holding position is impeded, and to release the latching device 306 from the catch 308 upon further rotation in the rotational direction such that a rotation in the opposite rotational direction beyond the holding position is again possible. The latching device 306 may thereby be either affixed to the support device 301 and the catch 308 to the image display unit 115 or, vice versa, the latching device 306 to the image display unit 115 and the catch 308 to the support device 301. The holding position is thereby either an intermediate position between the operating position and the rest position or, in an embodiment, the rest position itself. In a further embodiment, the locking device 312 may at least provides a further holding position between the rest position and the operating position.

Figure 4A:
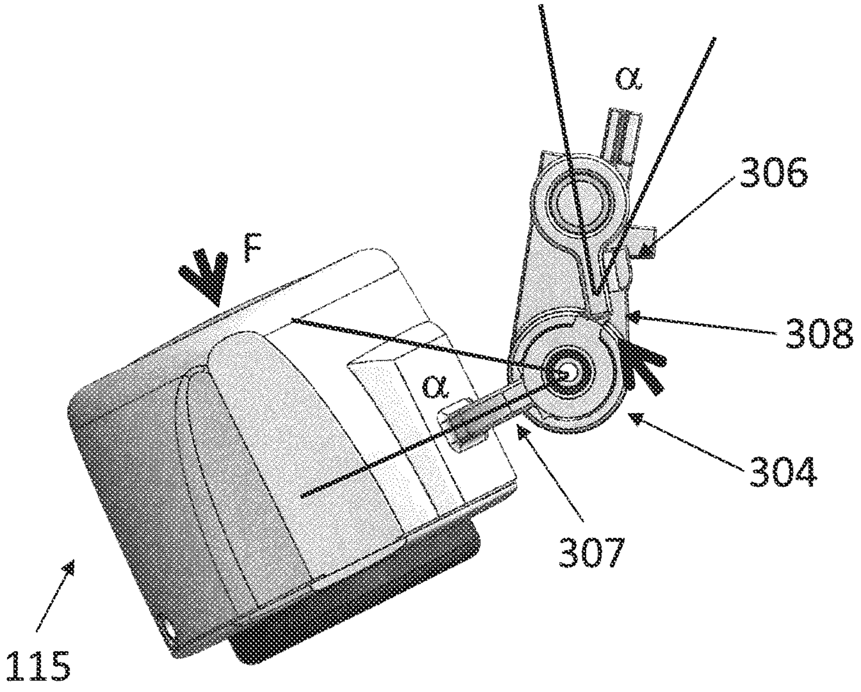
FIGS. 4A, 4B, 4C and 4D show a preferred embodiment of the inventive locking device of the video glasses in different positions.

In the following, the video glasses 300 according to the invention will be explained with reference to FIGS. 4A-D. FIGS. 4A-D show the locking device 312 in different positions. FIG. 4A shows the locking device 312 in the holding position as it comes to rest after rotation from the operating position into the rest position, which in the Figure corresponds a rotation clockwise. The latching device 306, here in an embodiment shown as biased and rotatable pin, is engaged in the catch 308. In an embodiment, the latching device 306 may be an elastic tongue, preferably integrally formed with the support device 301. The elasticity thereby applies the spring effect. In this embodiment, the catch 308 is formed as a nose projecting radially outward from the rotational axis 304 of the joint 302 and providing a notch at the tip. In the holding position, the latching device 306 is engaged in the notch as shown. The weight force F of the image display unit acts against this rotational direction. The catch 308 is supported against the latching device 306 (indicated by the arrow) and thus prevents a rotation of the image display unit 115 back in the direction of the operating position beyond the holding position. In the Figure, this corresponds to a rotation counterclockwise about the rotational axis 304.

Figure 4B:
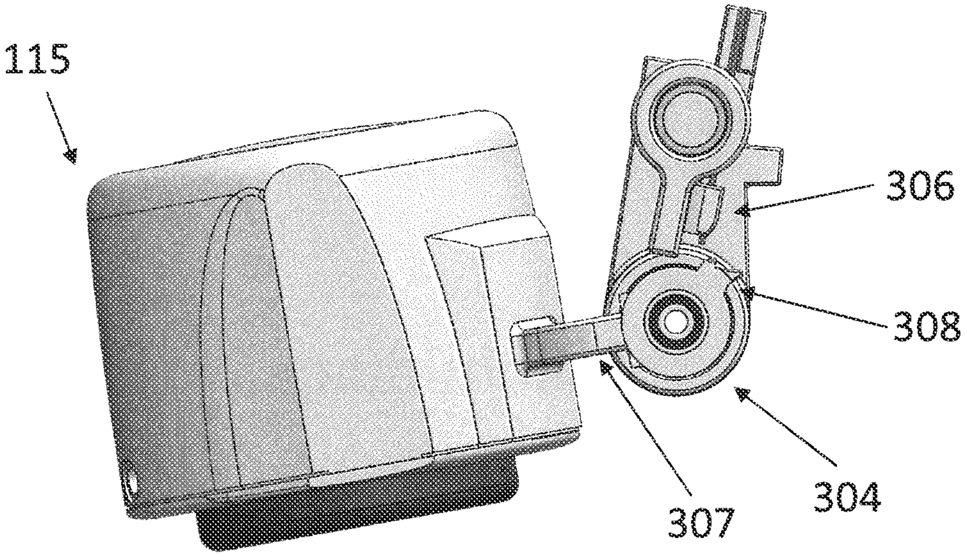
Figure 4C:
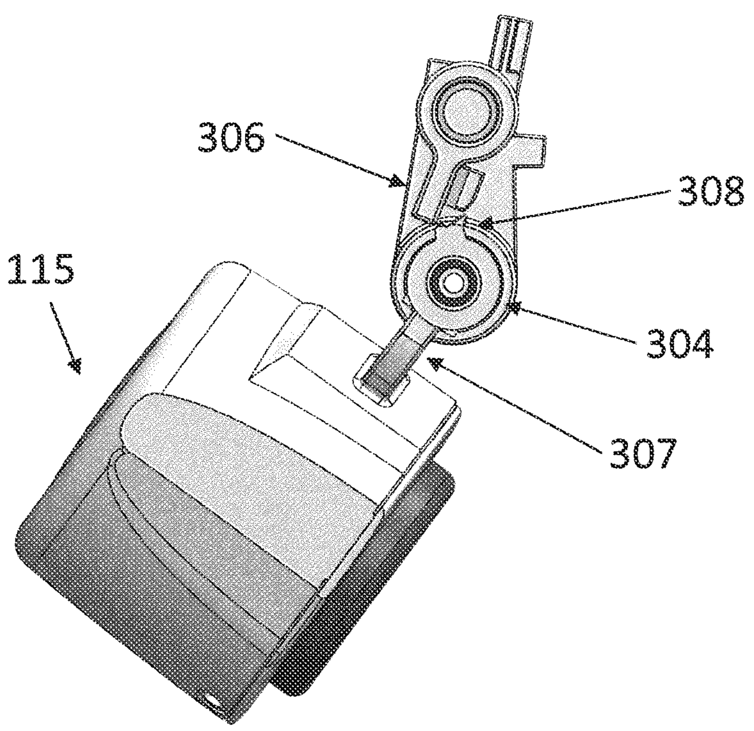
Figure 4D:
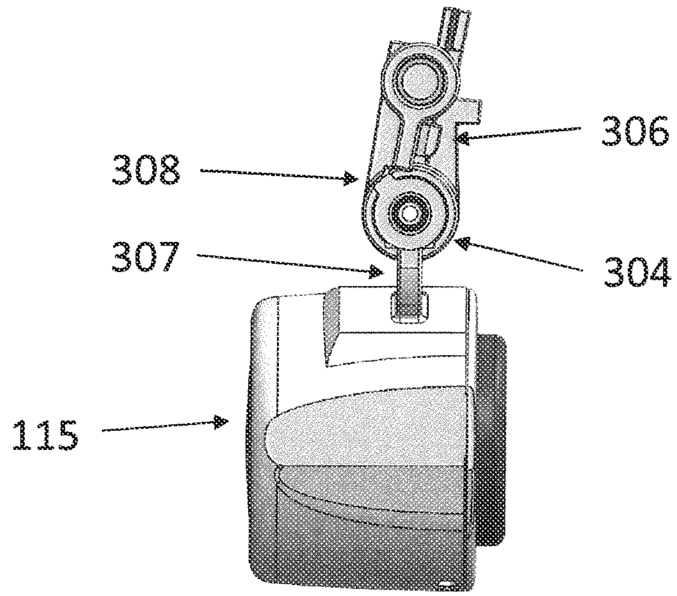

FIG. 4B shows the locking device 312 upon further rotation in the rotational direction, corresponding in the Figure to a rotation clockwise. The latching device 306 initially remains in the catch 308. Only after the rotation is further rotated beyond an angle α, the latching device 306 is released again from the catch 308. In a preferred embodiment, the angle α is about 10°, 15° or in the range of 10° to 15°. If now rotated counterclockwise, as illustrated in FIG. 4C, the latching device 306 will mesh the catch 308 from the opposite side and engage. Accordingly, the catch 308 is only again supported against the latching device 306 upon rotation in the opposite rotational direction. In the Figure, this is a rotation clockwise. Upon further rotation counterclockwise, the latching device 306 is again released from the catch 308 and a further rotation about the rotational axis 304 of the joint 302 may take place without restrictions until the image display unit 115 returns again to the operating position. This position is shown in FIG. 4D. If the image display unit 115 is again rotated towards the rest position by rotation about the rotational axis 304, the locking device 312 is returned to the holding position as shown in FIG. 4A.

Figure 5:
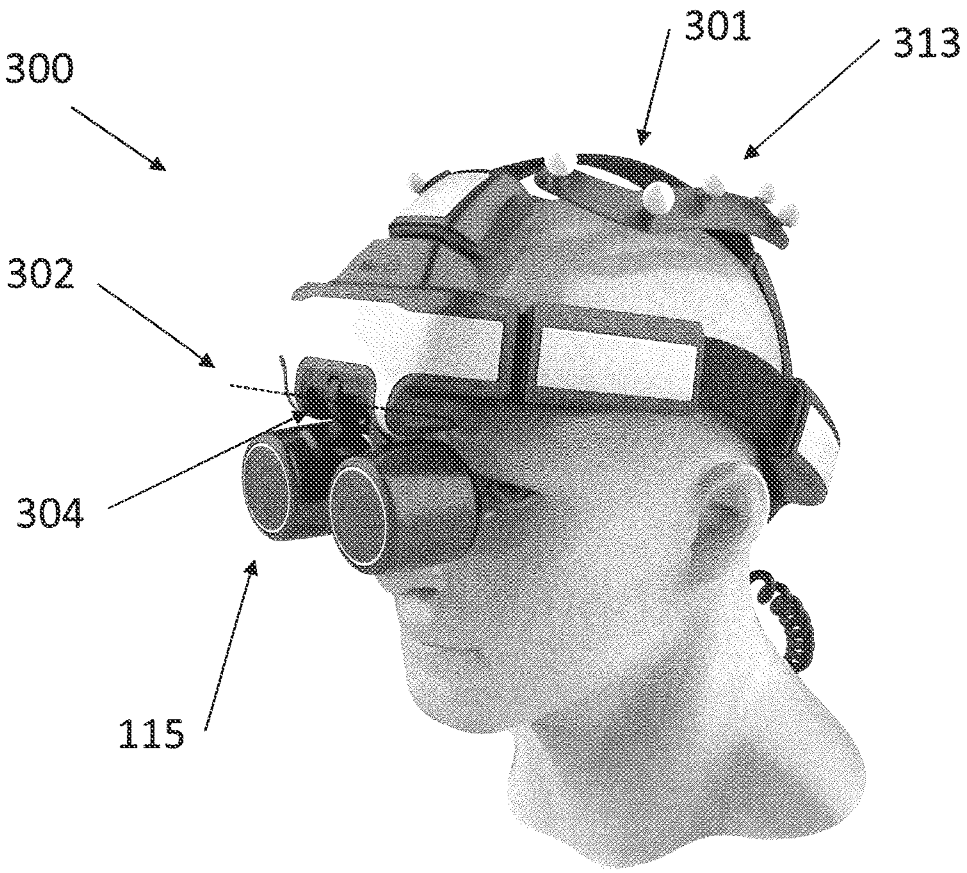
FIG. 5 shows a 3D-view of the video glasses according to the invention in an embodiment.

FIG. 5 shows an embodiment of the video glasses 300 according to the invention comprising a support device 301, an image display unit 115, a joint 304 with the rotational axis 302 and an optical marking 313 at a predetermined positions on the video glasses 300 for detection of the spatial orientation of the video glasses 300 by the detection device 104. The marks may be, for example, colored or in the infrared range reflective dots, lines or other symbols recognizable by image recognition. The rotational axis 302 is in parallel to the forehead of the user 103 when the video glasses 300 are worn. The image display unit 115 is arranged in front of the eyes of the user 103 in the operating position. If the image display unit 115 with the joint 304 is upwardly rotated about the rotational axis 302, the image display unit comes to rest in the rest position above the eyes and out of the visual field of the user 103. Further, in this position, the video glasses 300 in this embodiment are in the holding position and the latching device 306 is engaged in the catch 308 of the locking device 312 and prevents a rotation towards the operating position beyond the holding position, which, in this case, is also the rest position. The image display unit 115 is thereby held stably in the rest position. In order to return the image display unit 115 again in the operating position, the image display unit 115 has first to be raised upwardly beyond the rest position either manually or with the electric drive 309 by rotating the joint 302 about the joint axis 304 until the latching device 306 is released from the catch 308. Only then, the image display unit 115 may be returned in the opposite rotational direction of the joint 304 about the rotational axis 302 into the operating position.

The invention claimed is:

1. Video glasses for use in microsurgical procedures, comprising:

a support device configured to fasten the video glasses to a head of a user, an image display unit for outputting images, a joint with a rotational axis, which connects the support device with the image display unit rotationally about the rotational axis between an operating position, in which the image display unit is arranged in front of the eyes of the user and images can be displayed to the user, and a rest position, in which the image display unit is arranged upwards out of the visual field of the user, and a locking device comprising a latching device and a catch arranged to let the latching device upon rotation in a certain rotational direction about the rotational axis engage the catch in a holding position and to release the latching device from the catch upon further rotation in the certain rotational direction beyond the holding position, and wherein a rotation in the opposite rotational direction beyond the holding position is impeded as long as the latching device is engaged in the catch and the latching device has not been released from the catch upon further rotation in the certain rotational direction, wherein the release of the latching device from the catch having engaged the catch upon rotation in the certain rotational direction can only be achieved through further continued rotation in the certain rotational direction beyond the holding position, and not through any movement in the opposite rotational direction, and wherein the locking device prevents unintended movement of the image display unit from the rest position during surgical procedures by requiring the further continued rotation before the release.

2. The video glasses according to claim 1, wherein the holding position corresponds to the rest position, such that when the latching device engages the catch in the holding position, the image display unit is held stably in the rest position above the eyes and out of the visual field of the user.

3. The video glasses according to claim 1, wherein the locking device comprises at least a further holding position between the rest position and the operating position.

4. The video glasses according to claim 1, wherein the rotational angle from the holding position until release of the latching device from the catch is at least 10°.

5. The video glasses according to claim 1, wherein the rotational angle from the holding position until release of the latching device from the catch is not more than 15°.

6. The video glasses according to claim 1, wherein the latching device is configured as an elastically deformable tongue.

7. The video glasses according to claim 6, wherein the elastic tongue is integrally made of plastic with the support device.

8. The video glasses according to claim 1, wherein the latching device comprises a pin biased by a spring and being rotationally supported.

9. The video glasses according to claim 1, wherein the locking device is configured to only impede rotation in a direction from the rest position towards the operating position when the latching device is engaged with the catch.

10. The video glasses according to claim 9, wherein the latching device comprises a pin rounded at one side and the catch is configured to let the rounded pin slide off the catch upon rotation in the opposite rotational direction.

11. The video glasses according to claim 1, wherein the catch comprises a notch.

12. The video glasses according to claim 11, wherein the notch is applied at a tip of a nose.

13. The video glasses according to claim 1, wherein the joint comprises a parallelogram joint.

14. The video glasses according to claim 1, wherein the video glasses comprise an orientation sensor connectable to the video glasses.

15. Stereoscopic microscope comprising video glasses according to claim 1.

16. The video glasses according to claim 1, wherein the locking device is configured to maintain stable positioning of the image display unit during rapid head movements of a surgeon performing microsurgical procedures.

17. The video glasses according to claim 1, wherein the locking device requires a two-stage release sequence comprising:

(i) continued rotation beyond the holding position by at least 10 degrees in the certain rotational direction to disengage the latching device from the catch, and (ii) only then permitting rotation in the opposite direction toward the operating position.

18. Video glasses for use in microsurgical procedures, comprising:

a support device configured to fasten the video glasses to a head of a user, an image display unit for outputting images, a joint with a rotational axis, which connects the support device with the image display unit rotationally about the rotational axis between an operating position, in which the image display unit is arranged in front of the eyes of the user and images can be displayed to the user, and a rest position, in which the image display unit is arranged upwards out of the visual field of the user, and a locking device comprising a latching device and a catch arranged to let the latching device upon rotation in a certain rotational direction about the rotational axis engage the catch in a holding position and to release the latching device from the catch upon further rotation in the certain rotational direction beyond the holding position, and wherein a rotation in the opposite rotational direction beyond the holding position is impeded as long as the latching device is engaged in the catch and the latching device has not been released from the catch upon further rotation in the certain rotational direction, wherein the release of the latching device from the catch having engaged the catch upon rotation in the certain rotational direction can only be achieved through further continued rotation in the certain rotational direction beyond the holding position, and not through any movement in the opposite rotational direction, and wherein the locking device requires a two-stage release sequence comprising:

(i) continued rotation beyond the holding position by at least 10 degrees in the certain rotational direction to disengage the latching device from the catch, and (ii) only then permitting rotation in the opposite direction toward the operating position.

* * * * *